US012175734B2

(12) United States Patent
Wang et al.

(10) Patent No.: US 12,175,734 B2
(45) Date of Patent: Dec. 24, 2024

(54) CT BIG DATA FROM SIMULATION, EMULATION AND TRANSFER LEARNING

(71) Applicant: RENSSELAER POLYTECHNIC INSTITUTE, Troy, NY (US)

(72) Inventors: Ge Wang, Loudonville, NY (US); Daniel David Harrison, Delanson, NY (US); Xun Jia, Dallas, TX (US); Klaus Mueller, New York, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 1079 days.

(21) Appl. No.: 16/969,072

(22) PCT Filed: Feb. 11, 2019

(86) PCT No.: PCT/US2019/017476
§ 371 (c)(1),
(2) Date: Aug. 11, 2020

(87) PCT Pub. No.: WO2019/157435
PCT Pub. Date: Aug. 15, 2019

(65) Prior Publication Data
US 2021/0035340 A1 Feb. 4, 2021

Related U.S. Application Data

(60) Provisional application No. 62/629,464, filed on Feb. 12, 2018.

(51) Int. Cl.
| | |
|---|---|
| *G01N 33/48* | (2006.01) |
| *A61B 5/00* | (2006.01) |
| *G06F 18/214* | (2023.01) |
| *G06N 3/04* | (2023.01) |
| *G06N 3/08* | (2023.01) |
| *G06N 3/10* | (2006.01) |
| *G06N 20/00* | (2019.01) |
| *G06T 11/00* | (2006.01) |
| *G06V 10/82* | (2022.01) |

(52) U.S. Cl.
CPC ............ *G06V 10/82* (2022.01); *A61B 5/0033* (2013.01); *G06F 18/214* (2023.01); *G06N 3/04* (2013.01); *G06N 3/08* (2013.01); *G06N 3/10* (2013.01); *G06N 20/00* (2019.01); *G06T 11/006* (2013.01)

(58) Field of Classification Search
None
See application file for complete search history.

(56) References Cited

U.S. PATENT DOCUMENTS

| 2017/0103532 A1 | 4/2017 | Ghesu et al. |
| 2017/0148226 A1 | 5/2017 | Zhang et al. |

OTHER PUBLICATIONS

Bastos, Leonardo S., and Anthony O'Hagan. "Diagnostics for Gaussian Process Emulators." Technometrics 51.4 (2009): 425.*
Betechuoh, Brain Leke, Tshilidzi Marwala, and Thando Tettey. "Autoencoder networks for HIV classification." Current Science (00113891) 91.11 (2006).*
Le, Tuan Anh, Maximilian Igl, Tom Rainforth, Tom Jin, and Frank Wood. "Auto-encoding sequential monte carlo." arXiv preprint arXiv:1705.10306 (2017).*
International Search Report and The Written Opinion of the International Searching Authority, International Application No. PCT/US2019/017476, mailed Apr. 30, 2019.
Mustafa, M., et al., "Creating Virtual Universes Using Generative Adversarial Networks," Cornell University Library, Astrophysics, Instrumentation and Methods for Astrophysics, pp. 1-8, Jun. 7, 2017.
Chen, H., et al., "Low-Dose CT with a Residual Encoder-Decoder Convolutional Neural Network (RED-CNN)," Cornell University Library, Physics, Medical Physics, pp. 1-12, Feb. 1, 2017.

* cited by examiner

*Primary Examiner* — Anna Skibinsky
(74) *Attorney, Agent, or Firm* — Barclay Damon LLC; Anthony P. Gangemi

(57) ABSTRACT

In some embodiments, a method of machine learning includes identifying, by an auto encoder network, a simulator feature based, at least in part, on a received first simulator data set and an emulator feature based, at least in part, on a received first emulator data set. The method further includes determining, by a synthesis control circuitry, a synthesized feature based, at least in part, on the simulator feature and based, at least in part, on the emulator feature; and generating, by the auto encoder network, an intermediate data set based, at least in part, on a second simulator data set and including the synthesized feature. Some embodiments of the method further include determining, by a generative artificial neural network, a synthesized data set based, at least in part, on the intermediate data set and based, at least in part, on an objective function.

20 Claims, 3 Drawing Sheets

CT BIG DATA FROM SIMULATION, EMULATION AND TRANSFER LEARNING

CROSS REFERENCE TO RELATED APPLICATION(S)

This application claims the benefit of U.S. Provisional Application No. 62/629,464, filed Feb. 12, 2018, which is incorporated by reference as if disclosed herein in its entirety.

GOVERNMENT LICENSE RIGHTS

This invention was made with government support under Grant U01 EB017140-01A1 awarded by the National Institutes of Health. The government has certain rights in the invention.

FIELD

The present disclosure relates to big data, in particular to, computed tomography (CT) big data from simulation, emulation and transfer learning.

BACKGROUND

Data-driven tomographic reconstruction is an emerging area with significant potential. While computer vision and image processing are exemplary successes with machine learning/deep learning, tomographic reconstruction represents a next frontier of deep learning. In contrast to computer vision and image processing that analyze existing images, tomographic reconstruction produces images of internal structures from indirect data. Deep learning techniques are being developed for tomographic reconstruction worldwide with encouraging results. However, there are major challenges. First of all, a prerequisite for deep learning based reconstruction is the availability of big data. Unfortunately, clinical scans are generally unavailable to researchers due to patient privacy as well as proprietary considerations. For situations where clinical scans are available, a corresponding ground truth may be unavailable (e.g., four dimensional (4D) cardiac images, etc.) or sparse (e.g., experts' labeling is expensive and error-prone, and unsupervised learning remains relatively immature).

SUMMARY

In some embodiments, a method of machine learning includes identifying, by an auto encoder network, a simulator feature based, at least in part, on a received first simulator data set and an emulator feature based, at least in part, on a received first emulator data set. The method further includes determining, by a synthesis control circuitry, a synthesized feature based, at least in part, on the simulator feature and based, at least in part, on the emulator feature; and generating, by the auto encoder network, an intermediate data set based, at least in part, on a second simulator data set and including the synthesized feature.

Some embodiments of the method further include determining, by a generative artificial neural network, a synthesized data set based, at least in part, on the intermediate data set and based, at least in part, on an objective function.

In some embodiments of the method, the auto encoder network includes an input stage, an output stage and a latent space coupled between the input stage and output stage, the simulator feature and the emulator feature extracted from the latent space and the synthesized feature provided to the latent space.

In some embodiments of the method, the synthesized feature is determined based, at least in part, on at least one of a linear interpolation and/or an algebraic manipulation.

In some embodiments of the method, each data set is selected from the group including a computed tomography (CT) sinogram and a reconstructed CT image.

In some embodiments of the method, the objective function includes at least one parameter related to at least one of a physical characteristic, a physiological function and/or a model of a human organ.

In some embodiments, a transfer learning apparatus includes an auto encoder network and a synthesis control circuitry. The auto encoder network is configured to identify a simulator feature based, at least in part, on a received first simulator data set and an emulator feature based, at least in part, on a received first emulator data set. The synthesis control circuitry is configured to determine a synthesized feature based, at least in part, on the simulator feature and based, at least in part, on the emulator feature. The auto encoder network is further configured to generate an intermediate data set based, at least in part, on a second simulator data set and including the synthesized feature.

Some embodiments of the apparatus further include a generative artificial neural network configured to determine a synthesized data set based, at least in part, on the intermediate data set and based, at least in part, on an objective function.

In some embodiments of the apparatus, the auto encoder network includes an input stage, an output stage and a latent space coupled between the input stage and output stage, the simulator feature and the emulator feature extracted from the latent space and the synthesized feature provided to the latent space.

In some embodiments of the apparatus, the synthesized feature is determined based, at least in part, on at least one of a linear interpolation and/or an algebraic manipulation.

In some embodiments of the apparatus, each data set is selected from the group including a computed tomography (CT) sinogram and a reconstructed CT image.

In some embodiments of the apparatus, the objective function includes at least one parameter related to at least one of a physical characteristic, a physiological function and/or a model of a human organ.

In some embodiments, a machine learning system includes a simulator; an emulator; and a transfer learning circuitry. The transfer learning circuitry includes an auto encoder network and a synthesis control circuitry. The auto encoder network is configured to identify a simulator feature based, at least in part, on a received first simulator data set and an emulator feature based, at least in part, on a received first emulator data set. The synthesis control circuitry is configured to determine a synthesized feature based, at least in part, on the simulator feature and based, at least in part, on the emulator feature. The auto encoder network is further configured to generate an intermediate data set based, at least in part, on a second simulator data set and including the synthesized feature.

In some embodiments of the system, the transfer learning circuitry further includes a generative artificial neural network configured to determine a synthesized data set based, at least in part, on the intermediate data set and based, at least in part, on an objective function.

In some embodiments of the system, the auto encoder network includes an input stage, an output stage and a latent space coupled between the input stage and output stage, the simulator feature and the emulator feature extracted from the latent space and the synthesized feature provided to the latent space.

In some embodiments of the system, the synthesized feature is determined based, at least in part, on at least one of a linear interpolation and/or an algebraic manipulation.

In some embodiments of the system, each data set is selected from the group including a computed tomography (CT) sinogram and a reconstructed CT image.

In some embodiments of the system, the objective function includes at least one parameter related to at least one of a physical characteristic, a physiological function and/or a model of a human organ.

In some embodiments of the system, the simulator is a Monte Carlo simulator.

In some embodiments, a computer readable storage device has stored thereon instructions that when executed by one or more processors result in the following operations including any embodiment of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
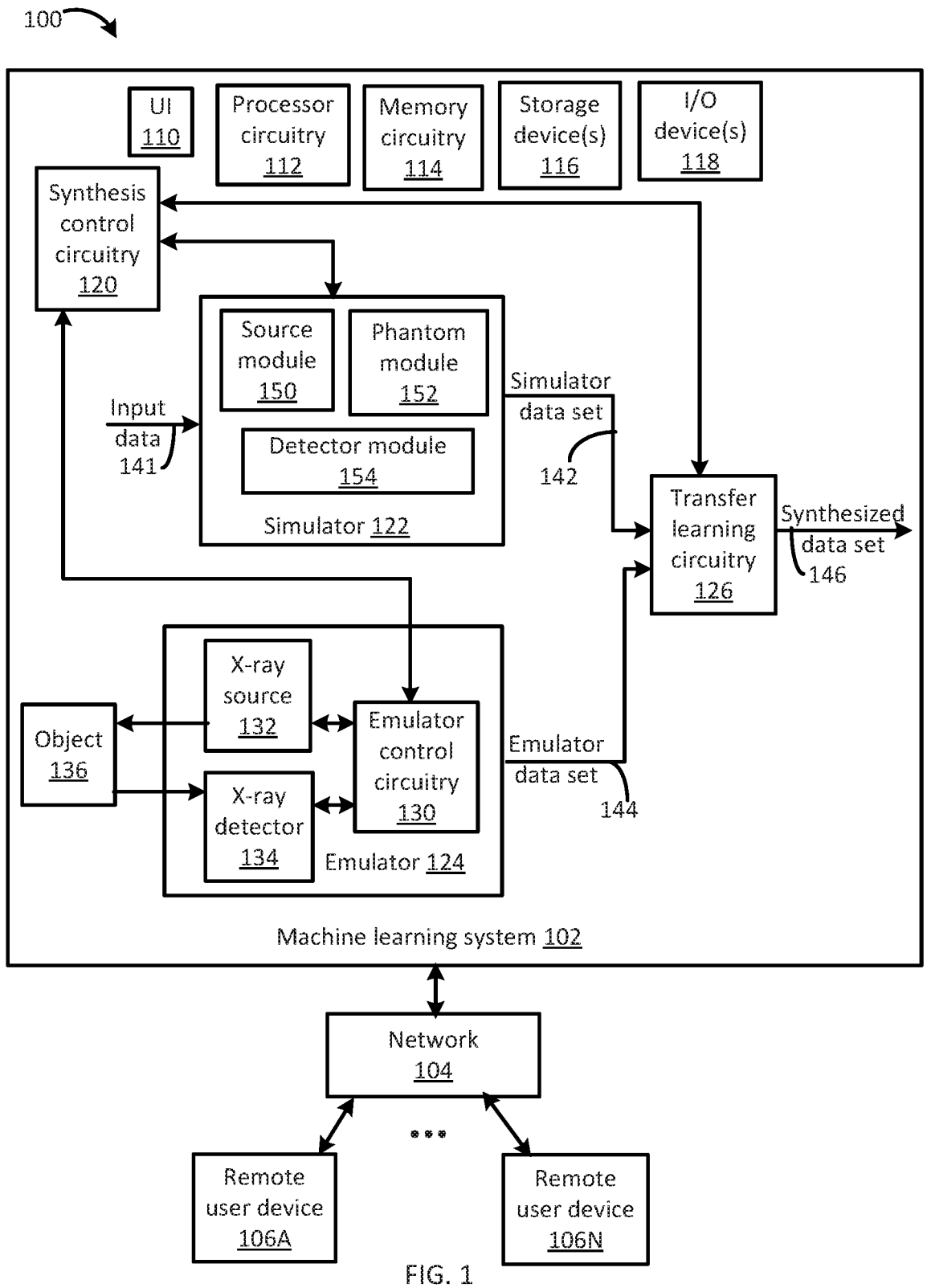
FIG. 1 illustrates a functional block diagram of a system that includes a machine learning system consistent with several embodiments of the present disclosure.

Machine learning may be utilized for tomographic reconstruction and radiomics. In one approach to machine learning, deep learning techniques may be utilized for, for example, tomographic imaging including x-ray computed tomography (CT). Deep learning based reconstruction and analysis is based, at least in part, on big data. To develop new CT technologies such as high-resolution or photon-counting detectors, clinical scans may not be available at the developmental stage.

For research purposes, simulation and emulation may be utilized in non-clinical settings. However, CT simulation alone may not capture all imaging physical features. CT emulation itself is relatively more expensive and may be unable to adequately mimic a patient's anatomical characteristics. A combination of simulation and emulation may be configured to produce relatively more physically and anatomically realistic data. In one nonlimiting example, a method, apparatus and/or system may be utilized for cardiac CT to achieve relatively fine spatial details, subtle contrast resolution, relatively high imaging speed and a relatively low radiation dose. Cardiac diseases remain the number one killer in the US and worldwide. As the population ages, the volume of coronary CT angiography examinations will steadily increase, suggesting a clinical need for a dedicated cardiac CT scanner. In the following, application to cardiac CT is described. It is contemplated that a method, apparatus and/or system may be applied to other applications, consistent with the present disclosure.

An artificial neural network (ANN) is a network of elements (e.g., nodes) configured to receive input, change their internal state (activation) according to that input, and produce output depending on the input and activation. The network is formed by connecting the output of selected nodes to the input of other nodes to form a directed, weighted graph. The weights as well as the functions that compute the activation can be modified by learning (e.g., training).

A deep neural network is an ANN that has a plurality of layers between the input and output layers. A relationship between the input and the output may be linear or non-linear. A convolutional neural network (CNN) is a type of deep, feed-forward ANN, that includes one or more convolutional layers with fully connected layers on top. A multilayer perceptron (MLP) is a type of feed-forward ANN that includes at least three layers of nodes and each node, except for the input nodes, uses a nonlinear activation function. An MLP may be trained using back propagation, a supervised learning technique. The multiple layers and non-linear activation of an MLP distinguish it from a linear perceptron. CNNs are a type of deep ANN that use a variation of multilayer perceptrons designed to use minimal preprocessing.

As used herein, the terms "neural network" and "artificial neural network" (ANN) correspond to an artificial neural network, a deep neural network, a convolutional neural network (CNN), a residual encoder-decoder CNN (RED-CNN), a generative adversarial network (GAN) and/or a multilayer perceptron.

Deep learning is a type of machine learning technique that uses a cascade of a plurality of layers of nonlinear processing units for feature extraction and transformation. Each successive layer uses the output from the previous layer as input. Deep learning techniques learn in supervised (e.g., classification) and/or unsupervised (e.g., pattern analysis) manners. Deep learning algorithms learn multiple levels of representations that correspond to different levels of abstraction. In other words, deep-learning methods are representation-learning methods with multiple levels of representation, obtained by composing simple but non-linear modules that each transform the representation at one level into a representation at a higher, slightly more abstract level. With the composition of enough such transformations, very complex functions can be learned.

Generally, the present disclosure relates to a method and/or system configured to facilitate machine learning. The method and/or system may be configured to generate big data from simulation, emulation and transfer learning. The big data may then be utilized to facilitate machine learning in, for example, tomographic imaging. "Big data" corresponds to orc the order of hundreds to an unlimited number of data sets. The data sets may include, but are not limited to, a CT sinogram, a reconstructed CT image, etc.

In an embodiment, a method of machine learning is provided. The method includes identifying, by an auto encoder network, a simulator feature based, at least in part, on a received first simulator data set and an emulator feature based, at least in part, on a received first emulator data set. The method further includes determining, by a synthesis control circuitry, a synthesized feature based, at least in part, on the simulator feature and based, at least in part, on the emulator feature. The method further includes generating, by the auto encoder network, an intermediate data set based, at least in part, on a second simulator data set and including the synthesized feature. In some embodiments, the method may further include determining, by a generative artificial neural network, a synthesized data set based, at least in part, on the intermediate data set and based, at least in part, on an objective function.

Thus, CT big data generated from a combination of simulation, emulation and transfer learning may approach real scans/images for deep reconstruction and deep radiomics. The techniques described herein may be applied to cardiac CT, and may be extended for other CT/photon-counting CT applications. A method, apparatus and/or system may be made available to one or more remote users via a user-friendly interface to allow a high-quality synthesis of various diverse yet plausible sinograms and image volumes. These data sets and images may enable extensive studies on motion artifact suppression, cardiac functional imaging, plaque characterization, radiation dose reduction, radiomics, etc. Such studies may no longer be constrained by a lack of actual clinical data.

FIG. 1 illustrates a functional block diagram of system 100 that includes a machine learning system 102 consistent with several embodiments of the present disclosure. System 100 further includes a network 104 and may include one or more remote user devices 106A, . . . and/or 106N. Network 104 may be included in and/or coupled to machine learning system 102. One or more remote user devices 106A, . . . and/or 106N may be coupled to machine learning system 102 via network 104.

Machine learning system 102 includes a user interface (UI) 110, processor circuitry 112, memory circuitry 114, one or more storages device(s) 116 and input/output (I/O) device(s) 118. UI 110 is configured to provide access to machine learning system 102 by one or more users. The users may directly access machine learning system 102 or may access machine learning system 102 using a remote user device, e.g., remote user device 106A, via network 104. Storage device(s) 116 may be configured to store data sets, as described herein. I/O device(s) 118 may be configured to couple machine learning system 102 to network 104 and, thus, to one or more remote user devices 106A, . . . and/or 106N.

Machine learning system 102 further includes synthesis control circuitry 120, simulator 122, emulator 124 and transfer learning circuitry 126. Synthesis control circuitry 120 is configured to manage machine learning operations, as described herein. Simulator 122 is configured to generate a simulator data set based, at least in part, on received input data, as will be described in more detail below. Emulator 124 is configured to generate an emulator data set based, at least in part, on object 136, as will be described in more detail below.

Processor circuitry 112 is configured to perform operations of machine learning system 102 including, for example, operations of synthesis control circuitry 120, simulator 122, emulator 124 and/or transfer learning circuitry 126. In an embodiment, processor circuitry 112 may include one or more graphics processing units (GPUs). For example, processor circuitry 112 may include a plurality of GPUs configured to operate in parallel. Such parallel operation is configured to increase the throughput of machine learning system 102.

Memory circuitry 114 may be configured to store information and/or data (e.g., input, simulator, emulator, intermediate, synthesized, output) and/or one or more parameters associated with simulator 122, emulator 124 and/or transfer learning circuitry 126. Storage devices 116 may be configured to store information and/or data input, simulator, emulator, intermediate, synthesized, output) and/or data sets generated as a result of operation of machine learning system 102.

Machine learning system 100 is configured to integrate simulation, emulation and transfer learning in a machine learning framework. In an embodiment, simulator 122 is configured to receive input data 141 and to generate a simulator data set 142 based, at least in part, on the received input data. In one nonlimiting example, the simulator data set 142 may correspond to a simulator CT data set. The simulator CT data set may include a simulator CT sinogram or a simulator CT image. Emulator 124 is configured to generate an emulator data set 144 based, at least in part, on the object 136. In one nonlimiting example, the emulator data set 144 may correspond to an emulator CT data set. The emulator CT data set may include an emulator CT sinogram or an emulator CT image.

Emulator 124 includes emulator control circuitry 130 and may include x-ray source 132 and x-ray detector 134. Emulator control circuitry 130 is configured to manage operation of emulator 124. In one nonlimiting example, x-ray source 132 may be configured to generate x-ray radiation and to transmit at least a portion of the x-ray radiation to object 136. Continuing with this example, x-ray detector 134 may then be configured to detect attenuated and/or scattered x-ray radiation. Characteristics of the detected x-ray radiation may then be related to x-ray radiation received by object 136 and/or characteristics of object 136 itself.

In one nonlimiting example, simulator 122 may correspond to a Monte Carlo CT simulator. Simulator 122 is configured to capture relatively major interactions between x-ray photons, biological tissues and hardware components. In an embodiment, simulator 122 may have a modular design and may include a source module 150, a phantom module 152 and a detector module 154. The source module 150 may be configured to generate one or more photons. The photons may then be transported through the phantom module 152 and recorded by the detector module 154.

In one nonlimiting example, the source module 150 may be configured to generate x-ray photons according to a user-defined fluence map and energy spectrum. The user-defined fluence map and/or energy spectrum may be included in input data 141. In another nonlimiting example, the source module 150 may include a phase-space format. Electron-photon transport simulation may be performed within an x-ray tube included in the source module 150. Simulator 122 may include coupled electron-photon transport under continuous geometry. The x-ray tube may be modeled with geometrical high-fidelity, simulating the x-ray production from electrons impinging onto the anode to x-rays through the collimator blades. Photons hitting a plane outside the blades will be recorded in a phase-space file, and used in simulation. Multiple phase-space files may be generated corresponding to different conditions/protocols, involving kVp setting, focal spot size and dynamics, etc.

The detector module 154 may be configured to model a detector response in terms of energy response coefficients for an energy-integrating detector. A detailed response function in both energy and spatial domains may be incorporated. Simulator 122 may be further configured to simulate x-ray to optical signal conversion, optical signal propagation and detection inside a detector, to determine detector response functions. Once these functions are determined, for a photon hitting on the x-ray detector array, the signals triggered in pixels may be determined using the response functions. To support simulations with photon-counting detectors, simulator 122 may include corresponding models (detector size, energy resolution, charge sharing, pileup, and other details). Different tally strategies may be implemented in the detector module 154 to enable recording of total deposit energy or individual events depending on the detector type.

The phantom module 152 may include a voxelized geometry and/or a continuous geometry. In one nonlimiting example, 3D objects may be modeled as a mesh representation. The mesh representation may be configured to represent dynamic heart phantoms. The photon transport simulation may be configured to accommodate the time-varying mesh representation. Voxelized geometry may be used to support modeling of visual human CT images and other volumetric atlases that are not in continuous geometry.

In an embodiment, the phantom module 152 may be configured to support simulations with diversified phantoms. For example, the phantom module 152 may include a pool of digital phantoms in a plurality of categories. Digital phantoms corresponding to physical phantoms to be scanned based on specified geometry and materials using meshed geometry may be generated and stored. Voxelized geometry may be utilized to represent real patient anatomy and select representative patient chest CT images from, for example, the Visible Human Project and/or other sources.

The digital phantom collection may further include actual clinical CT scans publicly available, for example, the MESA data sets and/or calcium scoring CT data sets from the patients in the Multi-Ethnic Study of Atherosclerosis (MESA) funded by NHLBI (National Heart, Lung and Blood Institute), including 6,814 patients who underwent CT for coronary artery calcification (CAC) scoring, and followed-up over 10 years to determine risk of CVD (cardiovascular disease). The de-identified MESA data sets carry information pertaining to all 422 observed cardiovascular events including 68 CVD deaths, 190 non-fatal myocardial infarctions, 15 resuscitated cardiac arrests, and 149 angina-triggered ICA.

To support a variety of data acquisition geometries and to generate diverse data sets, simulator 122 may be configured to facilitate transport simulations of different configurations. Virtual scan configurations including, but not limited to, source and detector trajectories with respect to the phantom, scan speed, acquisition frequency, source kVp, mAs, bowtie, filter, collimator, phantom, cardiac rate and phase, etc., may be user-specified (via, for example, UI 110 and/or remote user device(s) 106A, . . . , 106N). Simulations may be coordinated to generate projections configured to meet predefined specifications.

It may be appreciated that the simulation task is highly parallelizable and, thus, may utilize a plurality of GPUs, in parallel. For example, processor circuitry 112 may include a plurality of GPUs. Each task may be configured to simulate a number of x-ray projections on a segment of a user-specified trajectory. Each GPU may be responsible for a distinct segment. A Message Passing Interface may be utilized to coordinate these job, thus, ensuring load balancing among GPUs.

Simulated data sets may be processed into sinograms for image reconstruction. The same CT reconstruction techniques may be applied to both simulated sinograms and emulated sinograms. The image reconstruction techniques may include, but are not limited to, filtered backprojection, model-based iterative reconstruction and data-driven reconstruction, respectively.

Emulator 124 may be configured to utilize dynamic anthropomorphic heart phantoms so that a sufficient amount of diverse data sets can be produced with relevant physiological and pathological features.

In one nonlimiting example, x-ray source 132 may be configured with a 0.5 millimeter (mm) focal spot that can be pulsed and wobbled. Thus, x-ray source 132 may be configured to emulate not only regular but also high-resolution and high-speed cardiac CT scans with fully-controllable phantoms.

In one nonlimiting example, x-ray detector 134 may be configured to correspond to a full-size CT detector array. In another nonlimiting example, x-ray detector 134 may include photon-counting detector modules for general medical CT tasks. These photon-counting modules may be re-used for generation of CT big data. In another example, x-ray detector 134 may include photon-counting MARS detector modules featuring a relatively fine detector element pitch of down to 55 µm (micrometer). The detectors may be configured to emulate conventional, spectral and hybrid CT architectures. In one nonlimiting example, a photon-counting detector module may be embedded in the center of an energy-integrating detector array to offer a spectrally resolved region of interest (ROI) in a global gray-scale CT background.

Emulator 124 may be configured to implement various dynamic cardiac CT phantoms. For example, CIRS Cardiac Phantom dynamic cardiac phantom may be configured to emulate the realistic motion of a human heart. The CIRS Cardiac Phantom dynamic cardiac phantom is configured to provide accurate and repeatable 3D motion of a solid heart model inside the tissue-equivalent thorax phantom. CT images from this phantom can be analyzed with an associated image analysis tool for calcification detection, iodine contrast monitoring. ECG signal gating, and dosimetry. The cardiac phantom contains a motion actuator and a controller to steer the heart inside. Target pockets in the moving rod are configured to mimic the left coronary artery and posterior interventricular artery, and allow for placement of iodine contrast or calcification at different density levels. The 3D movement of the heart may be controlled by CIRS Motion Control program loaded with programmable motion profiles specific to different anatomical parts of the heart. The movement of the heart may be correlated with an ECG signal readable with cardiac monitoring devices, and adjustable in terms of amplitude, frequency, and phase.

In another example, an anthropomorphic heart phantom can be also obtained from Limbs & Things. Previous studies have demonstrated its use in cardiac CT and MRI assessment. Yet another anthropomorphic cardio CT phantom may be configured to provide a calibration standard for cardiac CT, and may be used for quantification of coronary artery calcifications. In another example, modern 3D-printing technology can also be used to create custom inserts to augment CT data sets.

The physical phantoms may be enhanced with animal tissues. Enhancement with animal tissues may provide more realistic hybrid anthropomorphic phantoms including inserts of calibrated contrast materials and ex vivo animal parts. The ex vivo animal parts and other customized parts may be independently scanned using a spectral micro-CT scanner to establish a gold standard.

Image reconstruction techniques may include, but are not limited to, detector-specific correction/fixing, normalization, log operation, etc. Filtered backprojection, model-based iterative reconstruction and data-driven reconstruction techniques may be utilized to reconstruct images from simulated, emulated and combined sinograms, respectively.

Thus, simulator 122 and emulator 124 may be configured to provide a variety of simulator data sets and emulator data sets. e.g., simulator data set 142 and emulator data set 144. In one nonlimiting example, each data set may correspond to a sinogram. In another nonlimiting example, each data set may corresponds to a reconstructed CT image. The simulator data sets and emulator data sets may then be provided to transfer learning circuitry 126.

In an embodiment, transfer learning circuitry 126 may correspond to an artificial neural network (ANN). In one nonlimiting example, transfer learning circuitry 126 may correspond to a generative adversarial network (GAN). In another nonlimiting example, transfer learning circuitry 126 may correspond to a Wasserstein GAN (WGAN). The WGAN may include gradient penalty. In another nonlimiting example, transfer learning circuitry may correspond to a knowledge assisted generative adversarial network (KAGAN). The KAGAN may be configured to incorporate prior knowledge information. Prior knowledge information may include, but is not limited to, a physical characteristic, a physiological function and/or a model of a human organ. The prior knowledge information may be related to one patient or a plurality of patients. In one nonlimiting example, the model may be a cardiac model.

Transfer learning circuitry 126 is configured to receive the simulator data set 142 and the emulator data set 144. Transfer learning circuitry 126 is then configured to generate at least one synthesized (i.e., output) data set 146 based, at least in part, on the simulator data set 142 and based, at least in part, on the emulator data set 144. In one nonlimiting example, the synthesized data set 146 may include an output sinogram. In another nonlimiting example, the synthesized data set 146 may include an output reconstructed CT image. Integrating simulation, emulation and transfer learning is configured to provide a relatively better quality output data set compared to the simulator data set or the emulator data set, alone.

Figure 2:
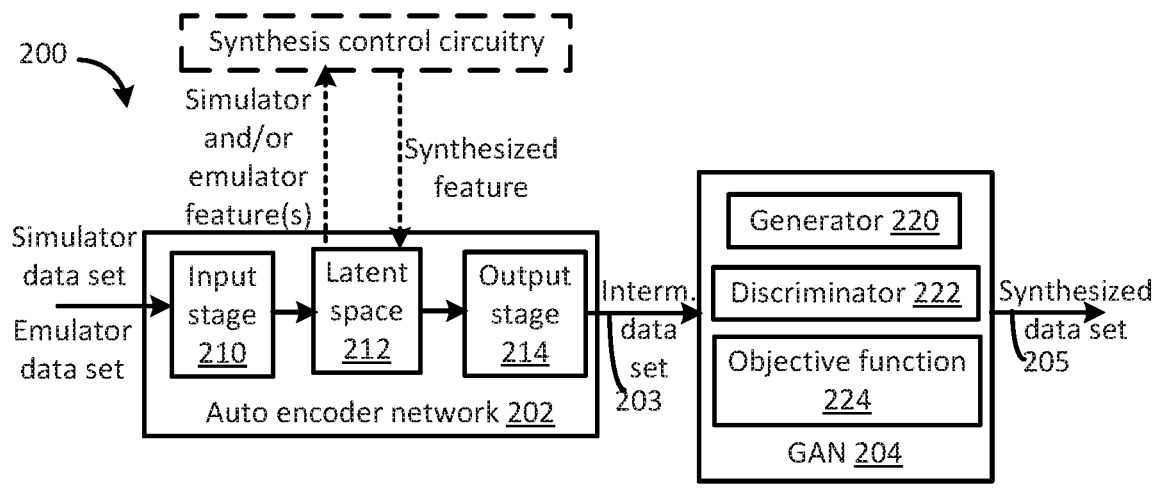
FIG. 2 illustrates a functional block diagram of a transfer learning circuitry consistent with one embodiment of the present disclosure.

FIG. 2 illustrates a functional block diagram of a transfer learning circuitry 200 consistent with one embodiment of the present disclosure. Transfer learning circuitry 200 is one example of transfer learning circuitry 126 of FIG. 1. Transfer learning circuitry 200 includes an auto encoder network 202 and a generative adversarial network (GAN) 204. The auto encoder network 202 is configured to receive a simulator data set and/or an emulator data set. For example, the simulator data set may be received from simulator 122 and the emulator data set may be received from emulator 124 of FIG. 1.

Auto encoder network 202 includes an input stage 210, a latent space 212 and an output stage 214. The latent space 212 is coupled between the input stage 210 and the output stage 214. The input stage 210 and the output stage 214 are configured to contain a same number of nodes (i.e., neurons). The latent space 212, also known as a "bottleneck", is configured to contain fewer nodes than the input stage 210 or the output stage 214. The reduced number of neurons of the latent space are configured to facilitate extraction of semantic information, i.e., features, from an input data set by the auto encoder network 202. For example, synthesis control circuitry 120 of FIG. 1 may be configured to extract one or more simulator features from latent space 212 when a first simulator data set is provided to auto encoder network 202. In another example, synthesis control circuitry 120 may be configured to extract one or more emulator features when an emulator data set is provided to auto encoder network 202.

Synthesis control circuitry 120 may be further configured to determine a synthesized feature based, at least in part, on a simulator feature and or an emulator feature. Determining the synthesized feature may include linear interpolation and/or algebraic manipulation. Operation on features identified in the latent space 212 may provide the benefit of manipulating relatively meaningful semantic features.

Figure 3:
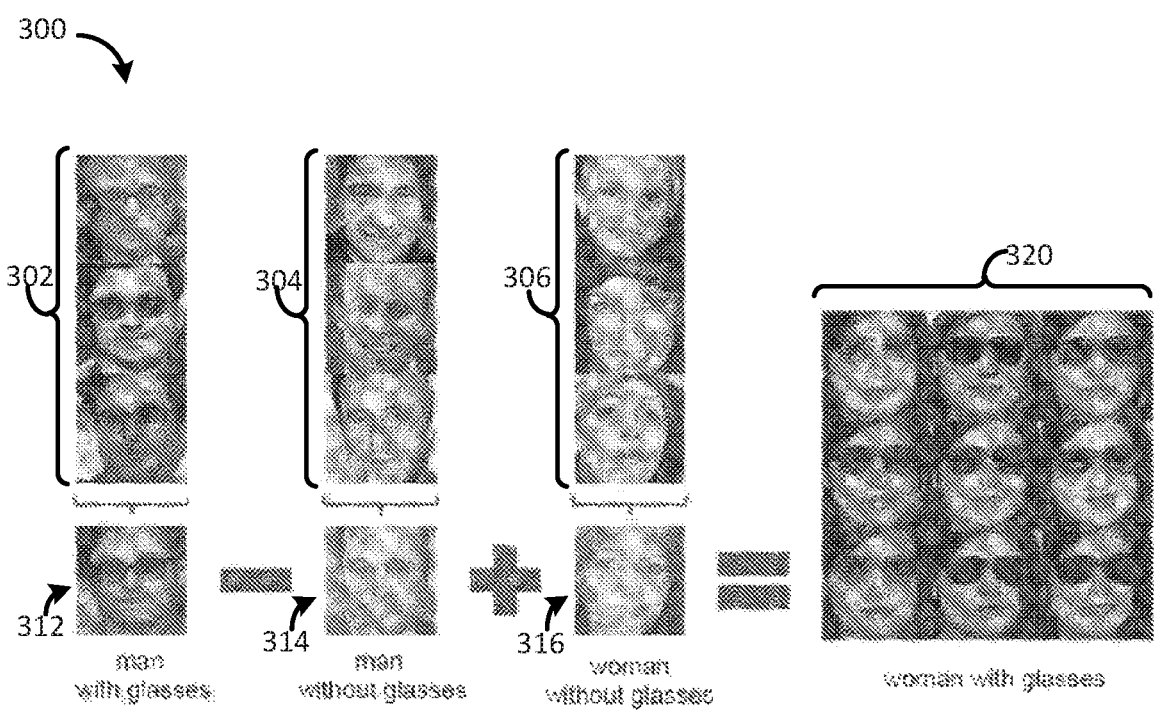
FIG. 3 illustrates one example of feature extraction and synthesis in a latent space.

FIG. 3 illustrates one example 300 of feature extraction and synthesis in a latent space. In this example 300, a set 302 of images of men with eyeglasses may correspond to an emulator data set and a set 304 of images of men without eyeglasses may correspond to a first simulator data set. A set 306 of images of women without eyeglasses may correspond to a second simulator data set. Image 312 corresponds to an average of the set 302 of images of men with eyeglasses and image 314 corresponds to an average of the set 304 of images of men without eyeglasses. Image 316 corresponds to an average of the set 306 of women without eyeglasses. An image of a woman with eyeglasses (center image in a set 320 of women with eyeglasses) may then be determined via algebraic manipulation in the latent space, e.g., latent space 212 of FIG. 2. The image of the woman with eyeglasses may correspond to an intermediate data set, as described herein.

Turning again to FIG. 2, the auto encoder network 202 may be configured to generate an intermediate data set 203 based, at least in part, on a second simulator data set and including a synthesized feature. In other words, a simulator feature may be determined based, at least in part, on the first simulator data set and a synthesized feature may be determined based, at least in part, on the simulator feature and based, at least in part, on an emulator feature. The second simulator data set and the synthesized feature may then be provided to the auto encoder network 202. The auto encoder network 202 may then generate the intermediate data set 203. One or more synthesized data sets 205 may then be generated by GAN 204 based, at least in part, on intermediate data set 203.

GAN 204 may include a generator 220, a discriminator 222 and an objective function 224. In one nonlimiting example, GAN 204 may correspond to a Wasserstein GAN. In another nonlimiting example, GAN 204 may correspond to a Wasserstein GAN with gradient penalty. In an embodiment, GAN 204 may correspond to a knowledge-assisted GAN (KAGAN). As used herein, a KAGAN corresponds to a Wasserstein GAN with an objective function that includes at least one parameter related to at least one of a physical characteristic, a physiological function and/or a model of a human organ. In one nonlimiting example, the model of a human organ may correspond to a cardiac model.

In an embodiment, the objective function 224 may correspond to a weighted sum of errors, similar to Allen's parameterization method in which simulated human body shapes with changing height and/or weight were generated from real body shapes. A body surface may be represented as a triangle mesh and three errors may be defined: a data error that corresponds to a distance between a template surface and a target surface, a smoothness error configured to constrain a smoothness between adjacent vertexes in the template surface and a marker error where markers correspond to anthropometric land markers on a human body prior to scanning. The objective function may then correspond to a weighted sum of these three errors. The constraints of physical characteristic(s), physiological function(s) and the model of a human organ are configured to yield clinically relevant images while providing a solution space large enough for diversified samples.

Thus, transfer learning circuitry 200 may be configured to receive a simulator data set from a simulator, e.g., simulator 122 of FIG. 1, and/or an emulator data set from an emulator, e.g., emulator 124, and to provide a synthesized data set as output. The auto encoder network 202 is configured to identify a simulator feature based, at least in part, on a received first simulator data set and an emulator feature based, at least in part, on a received first emulator data set. The synthesis control circuitry, e.g., synthesis control circuitry 120, is configured to determine a synthesized feature based, at least in part, on the simulator feature and based, at least in part, on the emulator feature. The auto encoder network is further configured to generate an intermediate data set based, at least in part, on a second simulator data set and including the synthesized feature. The generative artificial neural network 204 is configured to determine a synthesized data set based, at least in part, on the intermediate data set and based, at least in part, on an objective function.

Figure 4:
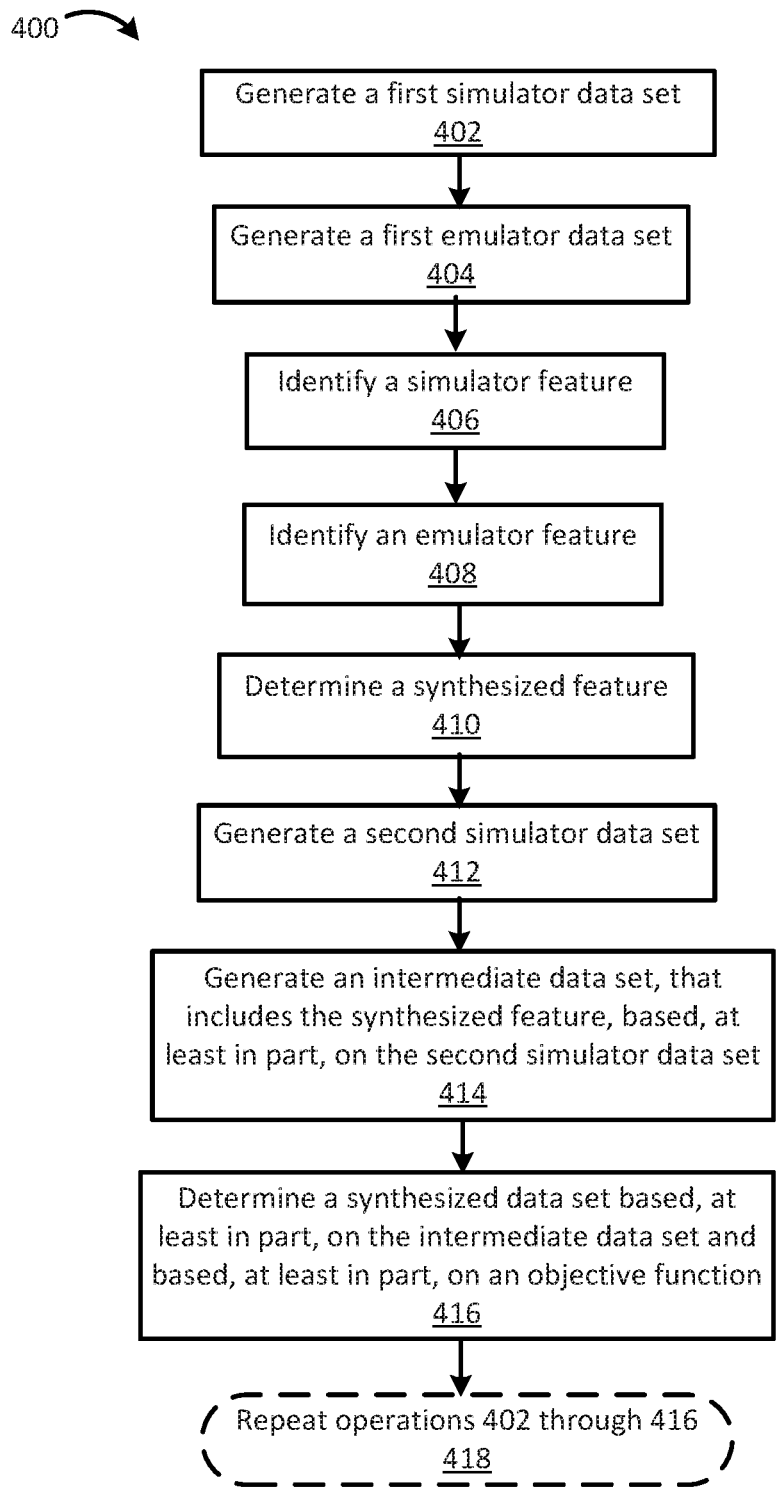
FIG. 4 is an example flowchart of machine learning operations consistent with several embodiments of the present disclosure.

FIG. 4 is an example flowchart 400 of machine learning operations consistent with several embodiments of the present disclosure. In particular, flowchart 400 illustrates generating a synthesized data set based, at least in part, on a simulator data set and based, at least in part, on an emulator data set. The operations of flowchart 400 may be performed by, for example, machine learning system 102 (e.g., synthesis control circuitry 120, simulator 122, emulator 124 and/or transfer learning circuitry 126) of FIG. 1 and/or auto encoder network 202 and/or GAN 204 of FIG. 2.

Operations of flowchart 400 may begin with generating a first simulator data set at operation 402. A first emulator data set may be generated at operation 404. Operation 406 may include identifying a simulator feature. Operation 408 may include identifying an emulator feature. A synthesized feature may be determined at operation 410. A second simulator data set may be generated at operation 412. An intermediate data set, that includes the synthesized feature, may be generated based, at least in part, on the second simulator data set, at operation 414. A synthesized data set may be determined based, at least in part, on the intermediate data set and based, at least in part, on an objective function, at operation 416. Operations 402 through 416 may be repeated at operation 418. Repeating operations 402 through 416 is configured to generate a plurality of synthesized data sets.

Thus, one or more synthesized data sets may be generated via transfer learning based, at least in part, on a simulator data set and based, at least in part, on an emulator data set.

Thus, a machine learning system, consistent with the present disclosure, is configured to integrate simulation, emulation and transfer learning. Such integration is configured to provide a relatively better quality output (i.e., synthesized) data set compared to the simulator data set or the emulator data set, alone.

While a machine learning system has been described herein relative to CT, it is contemplated that the idea can be extended to other imaging modalities and their combinations; such as magnetic resonance imaging, ultrasound imaging and simultaneous emission-transmission tomography.

As used in any embodiment herein, the term "logic" may refer to an app, software, firmware and/or circuitry configured to perform any of the aforementioned operations. As used in any embodiment herein, the term "module" may refer to an app, software, firmware and/or circuitry configured to perform any of the aforementioned operations.

Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Processor circuitry 112 may include, but is not limited to, a single core processing unit, a multicore processor, a graphics processing unit (GPU), a plurality of GPUs operating in parallel, a microcontroller, an application-specific integrated circuit (ASIC), a field programmable gate array (FPGA), a programmable logic device (PLD), etc.

Memory circuitry 114 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory circuitry 114 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-Ws), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method of machine learning, the method comprising:
   identifying, by an auto encoder network, a simulator feature based, at least in part, on a received first simulator computed tomography (CT) data set;
   identifying, by the auto encoder network, an emulator feature based, at least in part, on a received first emulator CT data set;
   determining, by a synthesis control circuitry, a synthesized feature based, at least in part, on the simulator feature and based, at least in part, on the emulator feature; and
   generating, by the auto encoder network, an intermediate data set based, at least in part, on a second simulator CT data set and comprising the synthesized feature.

2. The method of claim 1, further comprising:
determining, by a generative artificial neural network, a synthesized CT data set based, at least in part, on the intermediate data set and based, at least in part, on an objective function.

3. The method of claim 1, wherein the auto encoder network comprises an input stage, an output stage and a latent space coupled between the input stage and output stage, the simulator feature and the emulator feature extracted from the latent space and the synthesized feature provided to the latent space.

4. The method of claim 1, wherein the synthesized feature is determined based, at least in part, on at least one of a linear interpolation and/or an algebraic manipulation.

5. The method of claim 1, wherein each data set is selected from the group comprising CT sinogram and a reconstructed CT image.

6. The method of claim 2, wherein the objective function comprises at least one parameter related to at least one of a physical characteristic, a physiological function and/or a model of a human organ.

7. A transfer learning apparatus comprising:
an auto encoder network configured to identify a simulator feature based, at least in part, on a received first simulator CT data set and an emulator feature based, at least in part, on a received first emulator CT data set; and
a synthesis control circuitry configured to determine a synthesized feature based, at least in part, on the simulator feature and based, at least in part, on the emulator feature,
the auto encoder network further configured to generate an intermediate data set based, at least in part, on a second simulator CT data set and comprising the synthesized feature.

8. The apparatus of claim 7, further comprising a generative artificial neural network configured to determine a synthesized CT data set based, at least in part, on the intermediate data set and based, at least in part, on an objective function.

9. The apparatus of claim 7, wherein the auto encoder network comprises an input stage, an output stage and a latent space coupled between the input stage and output stage, the simulator feature and the emulator feature extracted from the latent space and the synthesized feature provided to the latent space.

10. The apparatus according to claim 7, wherein the synthesized feature is determined based, at least in part, on at least one of a linear interpolation and/or an algebraic manipulation.

11. The apparatus according to claim 7, wherein each data set is selected from the group comprising a CT sinogram and a reconstructed CT image.

12. The apparatus of claim 8, wherein the objective function comprises at least one parameter related to at least one of a physical characteristic, a physiological function and/or a model of a human organ.

13. A machine learning system comprising:
a simulator;
an emulator; and
a transfer learning circuitry comprising:
an auto encoder network configured to identify a simulator feature based, at least in part, on a received first simulator CT data set and an emulator feature based, at least in part, on a received first emulator CT data set; and
a synthesis control circuitry configured to determine a synthesized feature based, at least in part, on the simulator feature and based, at least in part, on the emulator feature,
the auto encoder network further configured to generate an intermediate data set based, at least in part, on a second simulator data set and comprising the synthesized feature.

14. The system of claim 13, wherein the transfer learning circuitry further comprises a generative artificial neural network configured to determine a synthesized CT data set based, at least in part, on the intermediate data set and based, at least in part, on an objective function.

15. The system of claim 13, wherein the auto encoder network comprises an input stage, an output stage and a latent space coupled between the input stage and output stage, the simulator feature and the emulator feature extracted from the latent space and the synthesized feature provided to the latent space.

16. The system according to claim 13, wherein the synthesized feature is determined based, at least in part, on at least one of a linear interpolation and/or an algebraic manipulation.

17. The system according to claim 13, wherein each data set is selected from the group comprising a CT sinogram and a reconstructed CT image.

18. The system of claim 14, wherein the objective function comprises at least one parameter related to at least one of a physical characteristic, a physiological function and/or a model of a human organ.

19. The system according to claim 13, wherein the simulator is a Monte Carlo simulator.

20. A computer readable storage device having stored thereon instructions that when executed by one or more processors result in the following operations comprising the method according to claim 1.

* * * * *